US012064371B2

(12) United States Patent
Oellgaard et al.

(10) Patent No.: US 12,064,371 B2
(45) Date of Patent: Aug. 20, 2024

(54) OSTOMY APPLIANCE HAVING AN ANTI-REFLUX COMPONENT

(71) Applicant: Coloplast A/S, Humlebaek (DK)

(72) Inventors: Claus Brennalt Oellgaard, Fredensborg (DK); Jesper Bruun Jensen, Soeborg (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 18/371,455

(22) Filed: Sep. 22, 2023

(65) Prior Publication Data

US 2024/0009022 A1  Jan. 11, 2024

Related U.S. Application Data

(63) Continuation of application No. 17/253,631, filed as application No. PCT/DK2019/050200 on Jun. 21, 2019, now Pat. No. 11,801,156.

(30) Foreign Application Priority Data

Jun. 21, 2018 (DK) .......................... PA 2018 70423

(51) Int. Cl.
 *A61F 5/44* (2006.01)
 *A61F 5/443* (2006.01)
 *A61F 5/445* (2006.01)
 *A61L 28/00* (2006.01)

(52) U.S. Cl.
 CPC ............ *A61F 5/4405* (2013.01); *A61F 5/445* (2013.01); *A61F 5/4407* (2013.01); *A61L 28/00* (2013.01)

(58) Field of Classification Search
 CPC ........ A61F 5/4405; A61F 5/445; A61F 5/443; A61F 5/4407
 See application file for complete search history.

(56) References Cited

U.S. PATENT DOCUMENTS

| 3,297,152 | A |   | 1/1967  | Corella et al. |
|-----------|---|---|---------|----------------|
| 3,405,714 | A |   | 10/1968 | Moss           |
| 3,780,739 | A |   | 12/1973 | Frank          |
| 4,084,590 | A | * | 4/1978  | Caraway ................. A61F 5/445 604/350 |
| 4,238,059 | A | * | 12/1980 | Caraway ............... A61F 5/4405 285/332 |

(Continued)

FOREIGN PATENT DOCUMENTS

| CN | 101040822 A | 9/2007 |
| CN | 101642413 A | 2/2010 |

(Continued)

OTHER PUBLICATIONS

Aura Urostomy, CliniMed®, clinimed.co.uk, May 11, 2013., http://web.archive.org/web/20130511044220/http://www.clinimed.co.uk/Stoma-Care/Products/Urostomy-Bags/Aura-Urostomy.aspx.

(Continued)

*Primary Examiner* — Guy K Townsend
(74) *Attorney, Agent, or Firm* — Coloplast Corp., Coloplast A/S; Nick Baumann

(57) ABSTRACT

An ostomy appliance has a waste collection container and an anti-reflux component disposed inside of the waste collection container. The anti-reflux component is connected to the top end portion of the waste collection container only above a center of an inlet opening for a stoma.

14 Claims, 5 Drawing Sheets

(56) References Cited

U.S. PATENT DOCUMENTS

| | | | | |
|---|---|---|---|---|
| 4,300,560 A * | 11/1981 | Steer | ............ | A61F 5/445 222/530 |
| 4,519,797 A * | 5/1985 | Hall | ............ | A61F 5/445 604/339 |
| 4,533,354 A | 8/1985 | Jensen | | |
| 4,604,095 A * | 8/1986 | Samuelsen | ............ | A61F 5/4405 604/350 |
| 6,352,526 B1 | 3/2002 | Cawood | | |
| 6,712,800 B2 * | 3/2004 | Kanbara | ............ | A61F 5/445 604/333 |
| 7,476,220 B2 * | 1/2009 | Lillegaard | ............ | A61F 5/4404 604/338 |
| 7,918,836 B2 | 4/2011 | Gill et al. | | |
| 8,764,716 B2 * | 7/2014 | Christensen | ............ | A61F 5/4405 604/326 |
| 9,119,727 B2 * | 9/2015 | Hannan | ............ | A61F 5/445 |
| 9,962,282 B2 * | 5/2018 | Chang | ............ | A61F 5/445 |
| 10,478,330 B2 * | 11/2019 | Wiltshire | ............ | A61F 5/445 |
| 11,224,535 B2 * | 1/2022 | Joh | ............ | A61F 5/449 |
| 11,559,425 B2 * | 1/2023 | Tretheway | ............ | A61F 5/441 |
| 11,801,156 B2 * | 10/2023 | Oellgaard | ............ | A61F 5/445 |
| 2003/0014023 A1 * | 1/2003 | Kanbara | ............ | A61F 5/445 604/333 |
| 2004/0064112 A1 | 4/2004 | Sun | | |
| 2006/0079854 A1 | 4/2006 | Kay et al. | | |
| 2009/0163883 A1 * | 6/2009 | Christensen | ............ | A61F 5/441 604/328 |
| 2011/0028924 A1 | 2/2011 | Murray | | |
| 2013/0053802 A1 * | 2/2013 | Maidl | ............ | A61F 5/445 604/332 |
| 2014/0163497 A1 * | 6/2014 | Hannan | ............ | A61F 5/443 156/60 |
| 2015/0190271 A1 * | 7/2015 | Chang | ............ | A61F 5/445 493/189 |
| 2021/0259874 A1 * | 8/2021 | Oellgaard | ............ | A61F 5/4405 |
| 2021/0369485 A1 * | 12/2021 | Evans | ............ | A61F 5/445 |
| 2021/0369493 A1 * | 12/2021 | Young | ............ | A61F 5/4404 |
| 2021/0369494 A1 * | 12/2021 | Holden | ............ | A61F 5/448 |
| 2024/0009020 A1 * | 1/2024 | Hansen | ............ | A61B 5/0002 |
| 2024/0009022 A1 * | 1/2024 | Oellgaard | ............ | A61F 5/4405 |

FOREIGN PATENT DOCUMENTS

| | | |
|---|---|---|
| CN | 103747764 A | 4/2014 |
| CN | 105682618 A | 6/2016 |
| GB | 2268882 B | 8/1996 |
| GB | 2539890 A | 1/2017 |

OTHER PUBLICATIONS

Flair®2 Urostomy Bag, Welland Medical, wellandmedical.com, Jun. 5, 2016., http://web.archive.org/web/20160605025737/https://wellandmedical.com/products/flair2-urostomy-bag/.

ConvaTec ActiveLife—Drainable 1-Piece Urostomy Pouch (Pre-cut), Express Medical Supply, Inc., exmed.net, Jul. 31, 2014., http:/web.archive.org/web/20140731055110/https://www.exmed.net/p-1476-convatec-activelife-drainable-1-piece-urostomy-pouch-pre-cut.aspx.

New Image Two-Piece Urostomy Pouch, Hollister®, hollister.com, Feb. 27, 2016, https://web.archive.org/web/20160227070609/http://www.hollister.com/en/products/Ostomy-Care-Products/Two-Piece-Pouching-Systems/Urostomy-Pouches/New-Image-Two-Piece-Urostomy-Pouch.

* cited by examiner

OSTOMY APPLIANCE HAVING AN ANTI-REFLUX COMPONENT

BACKGROUND

Stomal output often contains body fluids and visceral contents that are aggressive to both the skin of a user and to ostomy devices, in particular these have a detrimental effect on the efficiency and integrity of the adhesive materials that are applied to attach the ostomy device to the user's skin surface. Moreover, because such body fluids contain harsh substances they will quickly cause skin irritation, skin degradation and even wound creation in areas of the skin exposed to the substances.

Similar detrimental effects can be caused by urine, an issue particularly experienced by persons having a urostomy. A urostomy can be surgically created e.g. by ileal conduit urinary diversion, in which the ureter(s) are resected from the bladder and a ureteroenteric anastomosis is made to drain the urine into a detached section of the ileum (the small intestine). The end of the ileum is then brought out through an opening in the abdominal wall to form a stoma, from which urine exiting can be collected in a collecting device. Moreover, if collected urine can flow back (reflux) in the collecting bag and reach the area at the stoma, such as to persistently "flood" this area in urine, this can cause the stoma to close off and prevent continued delivery of urine. This is a serious condition which can lead to damages to the urinary system, including the bladder, and can ultimately be life-threatening.

For all types of users safe, reliable and efficient ostomy devices are highly desirable. Numerous attempts have been made to improve ostomy devices, e.g. to reduce leakage incidents from collecting bags or backflow of urine in collecting bags, to thereby mitigate the abovementioned issues and improve the wear time of the products. However, the provision of improvements to achieve better ostomy devices continues to be a focus area. Ostomists, health care professionals and manufacturers alike would welcome improvements in ostomy devices to make life easier for people with these types of intimate health care needs.

SUMMARY

The present disclosure provides aspects of a collecting bag including an anti-reflux component and of an anti-reflux component for a collecting bag according to the appended claims.

BRIEF DESCRIPTION OF THE DRAWINGS

The accompanying drawings are included to provide a further understanding of embodiments and are incorporated in and constitute a part of this specification. The figures illustrate embodiments and together with the description serve to explain principles of embodiments. Other embodiments and many of the intended advantages of embodiments will be readily appreciated as they become better understood by reference to the following detailed description.

Various exemplary embodiments and details are described hereinafter with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a specific embodiment is not necessarily limited to that embodiment and may be practiced in any other embodiments even if not so illustrated, or if not so explicitly described.

DETAILED DESCRIPTION

Figure 1:
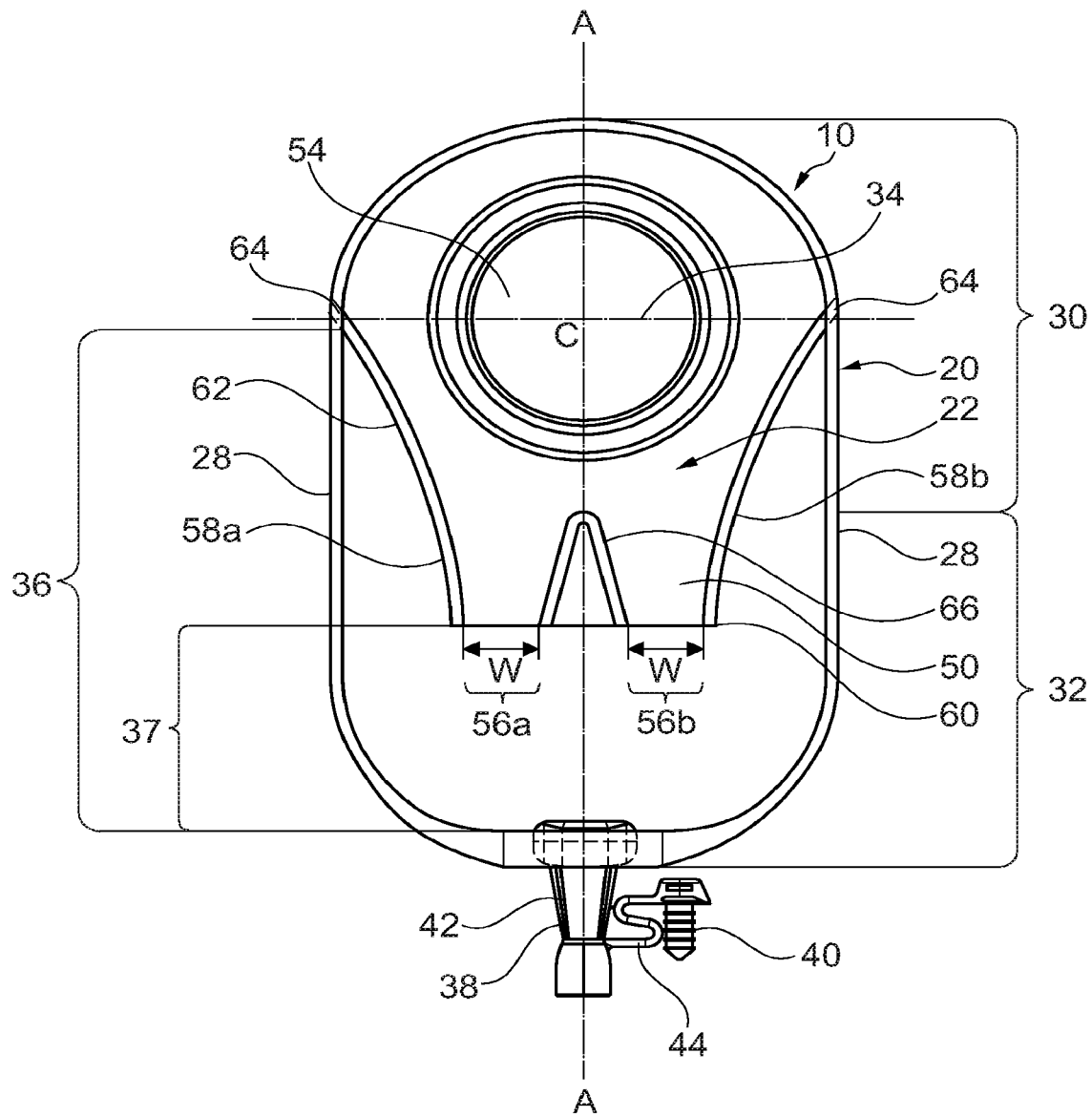
FIG. 1 is a top or plan view of one embodiment of a collecting bag of a urostomy appliance.

In the following Detailed Description, reference is made to the accompanying drawings, which form a part hereof, and in which is shown by way of illustration specific embodiments in which the invention may be practiced. In this regard, directional terminology, such as "top", "bottom", "front", "back", "leading", "trailing", etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that features of the various exemplary embodiments described herein may be combined with each other, unless specifically noted otherwise.

Throughout this disclosure, the words "(uro-) stoma" and "(ur-) ostomy" are used to denote a surgically created opening bypassing the intestines or urinary tract system of a person. The words are used interchangeably, and no differentiated meaning is intended. The same applies for any words or phrases derived from these, e.g. "(uro-) stomal", "(ur-) ostomies" etc. Also, the solid and liquid wastes emanating from the stoma may be referred to as stomal "output", "waste(s)", "liquid(s)" and "fluid(s)" etc. interchangeably. A subject having undergone ostomy surgery may be referred to as "ostomist" or "ostomate"—moreover, also as "patient" or "user". However, in some cases "user" could alternatively relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing or skin-closest side, when the ostomy appliance is worn by a user. Likewise, whenever referring to the distal side of a device or part of a device, the referral is to the side facing away or being farthest away from the skin, when the appliance is worn by a user. In other words, proximal is closest to the skin, when the appliance is fitted on a user and distal is the opposite—farthest away from the skin in use.

The axial direction is defined as the direction of a stoma, when the appliance is worn by a user (which in the real world may be a somewhat idealized notion, as all stomas look and behave individually—but for describing the disclosure, this designation is used). In an alternative wording, the axial direction is generally perpendicular to the skin or abdominal surface of the user.

The radial direction is defined as transverse to the axial direction that is transversely to the direction of the stoma. In relation to the radial direction, a reference to an "outer" element means that the element is radially farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The longitudinal direction should be understood in relation to the components of an ostomy appliance, such as a collecting bag, at least in a situation of use when it is worn by a user, such that the longitudinal direction of the appliance reflects its extent between a top end portion of the appliance, the top end portion being generally closer to the face of the user, and a bottom end portion being generally closer to the feet of the user.

The use of the phrase "substantially" as a qualifier to certain features or effects in this disclosure is intended to simply mean that any deviations are within tolerances, such as manufacturing tolerances, that would normally be expected by the skilled person in the relevant field.

The use of the word "generally" as a qualifier to certain features or effects in this disclosure is intended to mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The use of the word "essentially" as a qualifier to certain structural and functional features or effects in this disclosure is used for emphasizing what is the most important focus of something or fact about something—for example, a feature may have or fulfil a variety of effects, but when the disclosure discusses one effect as being "essentially" provided, this is the focus and the most important effect in relation to the present disclosure.

Collecting bags including means for preventing backflow of collected fluids, such as urostomy collecting bags including means for preventing backflow of urine, often designated anti-reflux or non-return means, are generally available on the market.

In such products, anti-reflux means or valves are typically provided by attaching one or more portions of the outer walls of a collecting bag to each other, i.e. by a 'direct' connection or attachment of the bag walls with each other. For such products, it has been found by experience that, as soon as any forces act on the collecting bag (inevitably arising from the user's movements and/or from interaction between the bag and the user's clothes and and/or from other influences), these forces create a pull or draw on the bag materials/components, which leads to wrinkling in or of the bag. Such wrinkling in turn causes pull and shear forces to act on the materials in a random and unpredictable manner, including at the anti-reflux means or valve, which consequently risk being pulled or drawn open or displaced, with the walls or sides of the means or valve shifted in relation to each other, and away from an otherwise general parallel, bordering ("kissing") relationship with each other.

Thus, in currently available products, such external forces are known to cause the valve means to be unintentionally pulled open, thereby diminishing or even totally restricting the anti-reflux (and thus sealing) effects of the anti-reflux valve means. This is at least partly because the only location on the device where such forces can be 'taken up' by the construction is where the materials are not connected or attached to each other, and consequently this tends to happen particularly at the anti-reflux means or valve. Such wrinkles, and the resulting unintended opening of the anti-reflux means valve, causes backflow or reflux of urine to happen. Such existing solutions are therefore found to be less satisfactory.

The "pulling apart" problem can occur in any kind and size of collecting bag applying a traditional anti-reflux or non-return valve, but has been found to be particularly intolerable in collecting bags for infants, including bags for prematurely born babies and/or infants having had stomal surgery (e.g. spina bifida patients). This is because this category of patients mostly lie down due to the treatment/surgery they have been/are undergoing, and they are consequently highly exposed to complications to the skin in case of backflow of urine or other stomal matter. Moreover, the skin of such infants is particularly susceptible to the influences of harsh stomal or urine fluids and they are also increasingly exposed to developing infections caused by external influences, such as bacteria in stomal fluids or urine.

To overcome the above listed issues, in one aspect, the present disclosure relates to a collecting bag configured to collect stomal fluids from a stoma of a user. Particularly, but not exclusively, in embodiments, the collecting bag is a urostomy collecting bag configured to collect urine from a urostomy of a user. The bag comprises first and second exterior bag walls attached to each other along a peripheral attachment zone. A longitudinal direction of the bag is defined between a top end portion of the bag and a bottom end portion of the bag. One of the first and second exterior bag walls comprises an inlet opening at the top end portion of the bag. A collecting volume of the bag is formed between the exterior bag walls. In embodiments, a major part of the collecting volume is configured at the bottom end portion of the bag. The top and bottom end portions of the bag, respectively, can be considered to border each other at an approximate midpoint of the bag, measured in the longitudinal direction of the bag.

The bag includes a drainage outlet provided at the bottom end portion of the bag. The drainage outlet is attached to one or both bag walls, and is configured to allow drainage of collected stomal fluids, such as urine. The drainage outlet is configured for repeated opening and closing events to allow drainage of collected stomal fluids, such as urine from the bag. In embodiments, the drainage outlet can include a valve of any suitable type.

The collecting bag includes an anti-reflux component attached to the bag. The anti-reflux component inside the bag formed by the first and second exterior bag walls. The anti-reflux component is configured to prevent reflux of collected stomal fluids, such as urine from the collecting volume to the inlet opening, i.e. to prevent the fluids from flowing back between the collecting volume and the inlet opening.

The anti-reflux component includes an interior, proximal contoured sheet comprising a receiving opening communicating with the inlet opening of the bag, and an interior, distal contoured sheet. The sheets of the anti-reflux component are connected to each other such as to define at least one passage between them towards the collecting volume. The passage has a width in a direction transverse to the longitudinal direction of the bag. The passage is configured to allow urine to exit the anti-reflux component and enter the collecting volume of the bag. In the sense of this disclosure, a sheet is a flat piece of film and/or foil and/or plastic. In embodiments a general thickness of a sheet is in the range of 10-150μ, such as 30-100μ, such as 50-80μ, such as 70μ. In embodiments, the sheet(s) can be formed of a laminated construction (a laminate). By providing the sheet(s) as a laminate, it is possible to further adapt the sheet(s) to fulfil different requirements such as being fluid tight, readily connectable to the other components (such as to be suitable for welding), odour retaining etc.

The sheets of the anti-reflux component are connected to further define two or more non-linear connection zones extending generally in the longitudinal direction of the bag from the at least one passage to the top end portion of the bag. In the sense of this disclosure, 'non-linear' should be understood in relation to an overall or general extent of the connection zone, meaning that minor portions of the connection zones 'locally' can be linear or straight or at least borderline linear. In embodiments, the non-linear connection zones are configured to define a peripheral contour of the anti-reflux component. In embodiments, the non-linear connection zones have a curved configuration in the longitudinal direction of the bag. In embodiments, each of the non-linear connection zones define at least a portion of a contour of the anti-reflux component. In embodiments, the non-linear connection zones define inverted arc-shapes in relation to each other.

A collecting bag including an anti-reflux component according to the disclosure provides a solution which prevents or at least greatly reduces the likelihood of wrinkling of the bag materials or components of the anti-reflux means or valve, thereby providing a safer, more reliable and more tight anti-reflux means. This in turn reduces or prevents stomal fluids, e.g. urine, from 'flowing back' within (inside) the collecting bag and thus reduces or prevents the detrimental effects of urine ending up on the user's skin surface, which detrimental effects are explained in the background section.

Among other objects, this disclosure provides a solution for an anti-reflux component particularly suitable for infants. In embodiments, the anti-reflux component is configured to prevent backflow of stomal fluids, e.g. urine, even if a child of up to at least 6 kg body weight is laying down and is laying on top of the collecting bag comprising the anti-reflux component. By lab tests, it has been shown that a urostomy collecting bag applying the anti-reflux component according to the disclosure provides satisfactory tightness to prevent the backflow of urine when exposed to external pressures, e.g. in a simulation test where it is exposed to the body weight of an infant. One measure for such satisfactory tightness is found to be that the anti-reflux component allows a maximum backflow or reflux of 1 mL/min of liquid measured over a five (5) min period (for testing purposes, the liquid used was water including a few drops of food colouring).

In aspects of the disclosure, these and other objects are fulfilled by providing an anti-reflux component comprising interior proximal and distal contoured sheets. The interior proximal and distal contoured sheets are connected to each other to form the anti-reflux component. In embodiments, a majority of a peripheral contour of the anti-reflux component is not connected or attached to the exterior bag walls of the collecting bag. By 'majority' is meant 50% or more of a total length of the peripheral contour of the anti-reflux component. In analogy, a 'minority' would be less than 50%. By not engaging a majority of the peripheral contour of the anti-reflux component with the exterior walls of the collecting bag, external forces acting on the exterior (outer) walls of the collecting bag are generally prevented from being transferred from the exterior walls to the sheets of the anti-reflux component. This construction helps prevent or at least greatly reduce wrinkling of the sheets of the anti-reflux component, which in turn secures that the passage of the anti-reflux component is not unintentionally pulled or drawn open by the externally acting forces. Thereby, the anti-reflux component of the disclosure provides increased security against backflow of liquid, such as urine, in a collecting bag, such as the urostomy collecting bag tested.

In embodiments, the anti-reflux component is attached to the collecting bag at a portion of the peripheral attachment zone at the top end portion of the bag. By attaching the anti-reflux component at a portion of the peripheral attachment zone at the top end portion of the collecting bag (as opposed to attaching the anti-reflux component along the edges of its contour in the longitudinal direction), the greatest possible extent of 'decoupling' (non-engagement) between the anti-reflux component and the exterior bag walls is achieved. This helps reduce or prevent the possibility of wrinkles being created in the passage of the anti-reflux component, because any forces acting on the exterior bag walls cannot be transferred to the sheets of the anti-reflux component. Additionally, this provides ease of manufacture of a collecting bag which includes an anti-reflux component according to the disclosure.

In embodiments, the anti-reflux component is attached to at least one of the first and second exterior bag walls at the peripheral attachment zone of the exterior bag walls, at a position being the same distance from the bottom edge of the anti-reflux component as the center of the inlet opening, measured in the longitudinal direction of the bag. In embodiments, the anti-reflux component is attached to at least one of the first and second exterior bag walls at the peripheral attachment zone of the exterior bag walls from the position being the same distance from the bottom edge of the anti-reflux component as the center of the inlet opening, and along an entirety of the peripheral attachment zone of the collecting bag being longitudinally 'above' the center of the inlet opening.

In embodiments, only a portion of a major surface of the interior, proximal contoured sheet (facing the "inside" of the exterior wall of the collecting bag) adjacent the receiving opening is attached to (the inside of) the exterior bag wall of the collecting bag. This attachment is around the inlet opening in the exterior wall. This provides for communication between the inlet opening and the receiving opening (i.e. for communication of stomal matter such as urine between the inlet opening in the exterior bag wall and the receiving opening of the anti-reflux component). In embodiments, the anti-reflux component is attached to an exterior bag wall of the collecting bag in a connection zone around the inlet opening in the exterior wall. In embodiments, the connection zone is arc-shaped. The feature 'arc-shaped connection zone' is intended to include a full circle or annular connection zone, as well as connection zone(s) formed as one or more discrete portion(s) of a circle or oval shape.

In embodiments, no portion of the peripheral contour of the anti-reflux component is attached to (at) the peripheral attachment zone of the exterior bag walls. In embodiments, the anti-reflux component is attached to one or both the first and second exterior bag walls in one or more discrete connection locations on a major surface of the distal and/or the proximal sheet (which surface should be understood to be configured to face towards an inside of the collecting bag). In embodiments, the anti-reflux component is attached on such a major surface of both the distal and the proximal sheet.

The non-linear connection zones of the anti-reflux component are provided at least at a portion of the total peripheral contour of the contoured sheets of the anti-reflux component. The non-linear connection zones extend from the passage, which passage is configured towards the collecting volume of the bag, and generally in the longitudinal direction to the top end portion of the bag, i.e. the zones extend "away" from the passage between the sheets towards the top of the bag. Along the non-linear connection zones the sheets of the anti-reflux component are not connected or attached to the exterior walls of the collecting bag. It has been found that the longer the distance from the passage of the anti-reflux component to any point or zone of attachment of the anti-reflux component with the peripheral attachment zone of the exterior bag walls, the lower the possibility of external forces acting on the exterior bag walls being transferred to the anti-reflux component. It is believed generally that the less connection or attachment between the exterior bag walls and the sheets of the anti-reflux component, the less wrinkling is created by external forces because they cannot be, or are largely prevented from being, transferred to the anti-reflux component. This reduces the risk of wrinkling of the anti-reflux component and therefore improves security against reflux.

In embodiments, the non-linear connection zones at the peripheral contour of the anti-reflux component are configured to provide a funnelling functionality of the anti-reflux component. Thereby, in use of the collecting bag, urine or stomal fluids entering the anti-reflux component at the receiving opening is guided to the passage towards the collecting volume by the funnelling effect of the non-linear connection zones under the influence of gravity.

In embodiments, the non-linear connection zones extend from a bottom edge of the anti-reflux component to a position being the same distance from the bottom edge of the anti-reflux component as a center of the inlet opening, measured in the longitudinal direction of the bag. This is to be understood such that the non-linear connection zones are configured to have the same longitudinal extent as an imaginary straight line extending between the midpoint of the inlet opening and the bottom edge of the anti-reflux component.

In embodiments, the anti-reflux component is configured to form an interior pouch inside first and second exterior bag walls of the collecting bag. Contrary to existing available collecting bags, in which the non-return means or valve forms a 'bridge' or bridging structure between the exterior walls of a collecting bag, the anti-reflux component of the disclosure forms an interior pouch located inside the collecting bag defined by the first and second exterior bag walls. In a sense, the anti-reflux component can be considered to form a 'bag-in-bag' structure.

In embodiments, the anti-reflux component is configured such that the sheets form an outer contour of the component (seen in the radial direction) being at least partially V- or funnel-shaped. It is to be understood then that a majority of the outer contour of the anti-reflux component is not attached to the peripheral attachment zone of the exterior bag walls of the collecting bag.

By providing an anti-reflux component as an interior pouch or bag-in-bag structure, the collecting bag of the disclosure can effectively be designed to include a collecting volume for urine or other stomal fluids, which can be a designated 'functional volume'. By this, it is meant that the collecting bag is configured to have a certain fill level at which the collected volume of urine or stomal fluids itself helps provide for ensuring tight closing of the passage of the anti-reflux component. This is achieved in the sense that urine or stomal fluids, held in the collecting volume defined by the first and second exterior walls of the collecting bag, provide(s) pressure on the outside surface of the sheets of the anti-reflux component at the passage. Thereby, the collected urine or stomal fluids assist(s) in providing a more secure closing of the anti-reflux component by pressing the sheets thereof towards each other to seal off the passage and prevent any reflux or backflow through the passage from the collecting volume. Depending on the specific application (or type) and dimensions of the collecting bag, the designated functional volume can be designed to have a certain size and/or maximum fill level. The provision of an interior pouch or bag-in-bag construction of the anti-reflux component in combination with one or more of the other attributed features of the anti-reflux component described herein, provides for establishing the designated functional volume and thereby the 'self-closing' effects of the anti-reflux component.

Other advantages achieved by embodiments of the anti-reflux component according to the disclosure when taking the form of an interior pouch of contoured sheets include keeping an area or zone of (adjacent to or near) the passage of the anti-reflux component ('the reflux area') at a maximum possible distance from the peripheral attachment zone of the first and second exterior bag walls. Further, the anti-reflux component provides for urine or stomal fluids to pass through the passage at a distance from the stoma, which helps increase security against backflow or reflux through the passages of the anti-reflux component. Moreover, the structure of the anti-reflux component in relation to the collecting bag is configured to ensure that only a minor volume of urine or stomal fluids can be held inside the anti-reflux component itself before it will begin to exit through the passage to the collecting volume of the bag. In addition, embodiments wherein the interior pouch or bag-in-bag structure of the anti-reflux component is only minimally connected or attached to the bag walls, ensure that there is sufficient space for a protruding stoma entering through the inlet- and receiving openings, with no or little possibility of the stoma interfering with the sheets of the anti-reflux component.

In embodiments, the sheets of the anti-reflux component combine to define two passages provided in a side-by-side relationship with each other in the transverse direction, separated by a center connection zone, in which center connection zone the sheets of the anti-reflux component are connected to each other. The center connection zone is provided to help control and guide the interior contoured sheets of the anti-reflux component to keep or remain in an optimum parallel relationship with each other at the passages, while simultaneously providing structure to the area ('reflux area') of the anti-reflux component at or adjacent the passages. Providing such structure in turn helps to ensure for the passages to readily and correctly open to allow urine or stomal fluids to pass from the anti-reflux component to the collecting volume of the bag, while also counteracting flow of urine or stomal fluids in the opposite direction.

In embodiments, a longitudinal extent of the center connection zone (i.e. in the longitudinal direction) is configured to be around 28 mm. In embodiments, the greater the longitudinal extent of the center connection zone, the more resistance and thus security against backflow there is in the 'reflux area'.

In embodiments, a distance between the anti-reflux component at a bottom edge thereof and the peripheral attachment zone of the first and second exterior bag walls, measured transverse to the longitudinal direction, is approximately 25 mm. In embodiments, this distance can be up to and including 70 mm. Depending on the required size and type of the collecting bag, the distance can advantageously be configured such that the 'reflux area' is the maximum possible distance away from the peripheral attachment zone of the first and second exterior bag walls. Maximizing this distance in relation to the collecting bag size (and/or collecting volume capacity) effectively provides an advantageous 'decoupling' of the anti-reflux component from the exterior walls of the collecting bag to a largest possible extent, thereby further helping to minimize wrinkling on the anti-reflux component caused by external forces acting on the exterior walls of the collecting bag.

In embodiments, a distance between the anti-reflux component at a bottom edge thereof and a portion of the peripheral attachment zone at or adjacent the drainage outlet at the bottom portion of the collecting bag is at least 52 mm. The larger this distance is, the greater the possible collecting volume of the bag. Too large of a collecting volume is not desirable because the weight of collected urine or stomal fluids can become too great and/or thereby make wearing of the collecting bag uncomfortable for the user. However, a further advantage of the anti-reflux component according to the disclosure is that the bag-in-bag solution allows for collected fluids to rise to a level (seen in the longitudinal direction) inside the outer bag located above a bottom edge of the anti-reflux component, thus the collecting volume is a 'functional volume'. Thereby, urine or stomal fluids, held in the outer bag, including in the collecting volume, provide(s) pressure on the outside surface of the sheets of the anti-reflux component at the passages, and thus functions to provide a more secure closing of the passages of the anti-reflux component, as explained in more detail above.

In embodiments, the center connection zone is configured to have a greatest extent transverse to the longitudinal direction at a bottom edge of the anti-reflux component and to gradually decrease in transverse extent towards the top end portion of the bag.

In embodiments, the center connection zone is configured to comprise two legs defined with an angle between them and meeting in a top area forming an upper limit point of the center connection zone towards the inlet and receiving openings in the longitudinal direction of the collecting bag (towards the upper end of the bag). In embodiments, an angle between the legs is acute. At a bottom edge of the anti-reflux component, the legs of the center connection zone terminate in bottom limit points with a distance between them. In embodiments, the sheets of the anti-reflux component at the center connection zone are connected or attached to each other only by the legs of the center connection zone. In other embodiments, the sheets are connected or attached to each other over an entirety of the center connection zone which is then defined by the area 'spanned' between the angled legs of the center connection zone from the upper limit point to the bottom limit points.

In embodiments, a width of the passage is configured to be at least 18 mm. In embodiments, the width of the passage is configured to be around 18 mm. A width of around 18 mm of the passage has been found to ensure a good flow of urine from the anti-reflux component and into the collecting volume of a urostomy collecting bag while simultaneously not being excessively or unnecessarily wide. In embodiments comprising more than one passage, each of the passages has a width of at least 18 mm. In embodiments comprising more than one passage, each of the passages has a width of around 18 mm.

In embodiments, the passage is configured to accommodate two urinary catheters of French size 10 (or CH 10). In some settings, it is a safety requirement of the product, and thus a criterion for health authority approval of a urostomy collecting bag, that a passage of a non-return valve allows for at least two CH 10 catheters to pass through. This is because in some surgical procedures it may be required to temporarily (such as over a matter of days to weeks) place a urinary catheter in each of the ureters leading urine from the kidneys to the bladder, and these catheters should then be able to drain into the collecting bag.

It is to be understood that in embodiments disclosed herein, the combined options, requirements and constraints on the different dimensions of the anti-reflux component and the collecting bag, particularly the dimensions and distances explained in the above, interplay with and influence each other, such that variation of the size of these dimensions to suit specific sizes or types of collecting bags, is intended to be included by the description and claims.

In embodiments, a drainage outlet is provided at a bottom end portion of the collecting bag. In embodiments, the drainage outlet is configured for repeated opening and closing events to allow draining of collected urine or stomal fluids from the collecting volume of the bag. In embodiments, the drainage outlet comprises a drain valve configured for repeated opening and closing events to allow drainage of collected urine or stomal fluids from the collecting volume. These options allow for the collecting bag according to the disclosure to be used also by physically 'active' (i.e. not only bed-ridden) users, as it allows the user him- or herself to control when to empty/drain the collected urine or stomal fluids, as opposed to continuous draining of the collected fluids from the collecting volume and into an output waste unit, such as a disposable night urine bag, which can be mounted on a patient bed.

In embodiments, the collecting bag further comprises means for attachment of the bag to the skin surface of a user. The collecting bag can include a one-piece appliance in which the collecting bag is permanently, or fixedly, secured to an adhesive base plate for attachment to the human skin, thus forming the attachment means. Alternatively, the collecting bag can be part of a two-piece appliance comprising a base plate and the collecting bag which are then configured be coupled and un-coupled from each other using suitable coupling means. The base plate of the two-piece appliance thus forms the attachment means.

The connection(s) between the different components of the disclosure, including the interior contoured sheets and the exterior bag walls can be suitably provided by welding, such as, but not exclusively, heat welding or heat sealing. Any suitable type of welding technique is acceptable. Alternatively, other connection methods are acceptable, e.g. including providing the connections by adhesive means.

Suitable materials for the proximal and distal interior contoured pieces of the anti-reflux component include EVA or PE and/or laminates thereof. A particularly suitable material for the proximal and distal interior contoured pieces of the anti-reflux component includes a 12% EVA/PE foil 70 μm (Ulfotene 96128) from the company Ulfoss, Holbæk, Denmark.

Suitable materials for the exterior bag walls of the collecting bag include gas- and liquid impermeable foil materials including polyethylenes (PE), polyvinyl-chlorides (PVC) and/or ethylene-vinyl-acetates (EVA). A particularly suitable material for the first and second exterior bag walls include MF713 (NMX0373), SA7ND, Clear, from the company Sealed Air GmbH, Norderstedt, Germany, which material is a co-extruded 7-layer film with six layers of EVA and a middle layer of PVdC.

DETAILED DESCRIPTION OF THE DRAWINGS

Figure 2A:
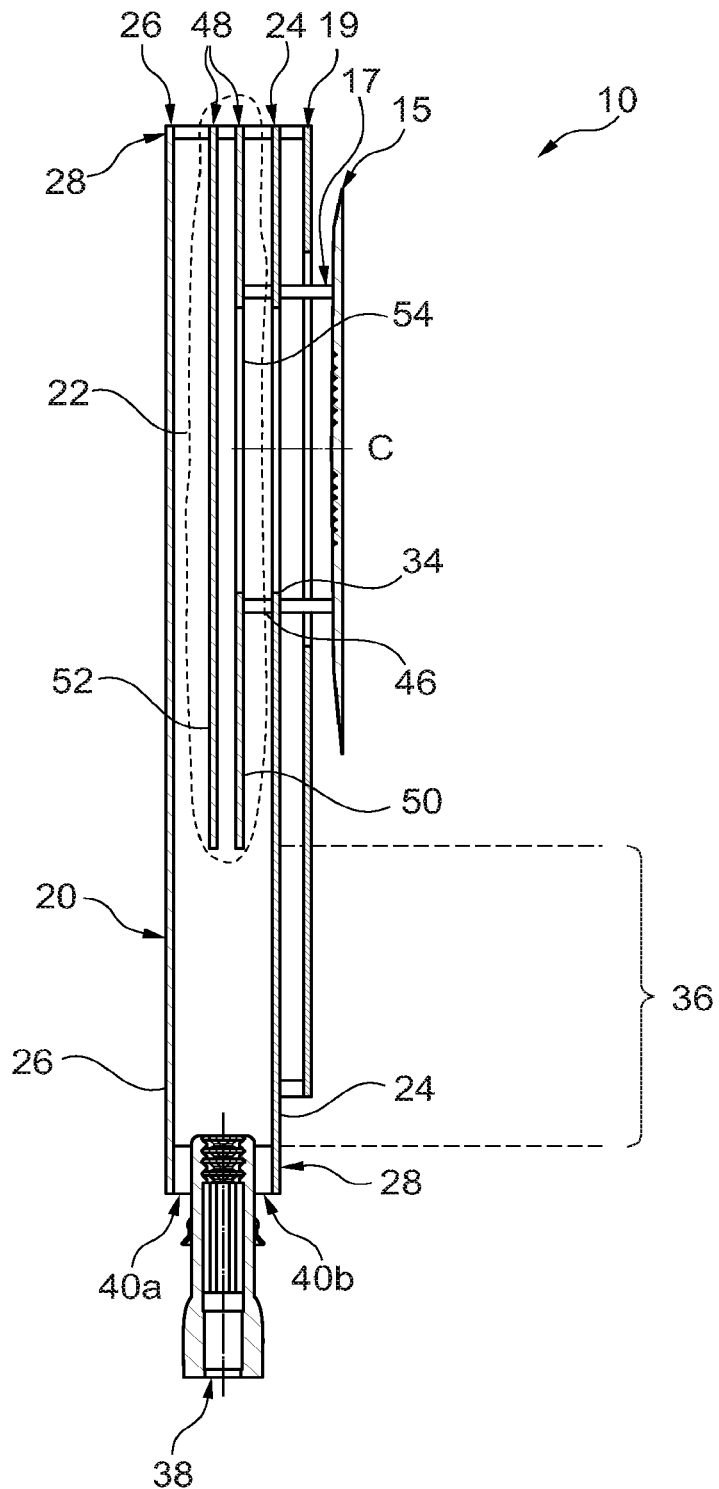
FIGS. 2A and 2B are cross-sectional views of one embodiment showing of a urostomy appliance.
Figure 2B:
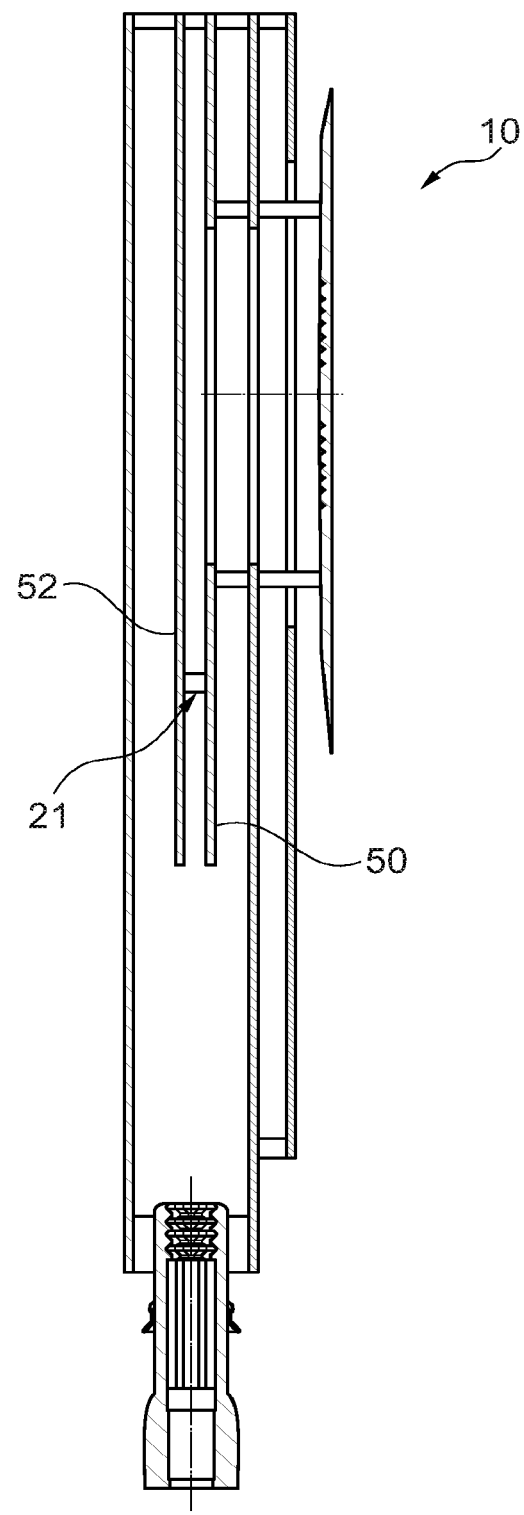

FIG. 1 is a sketched plane view and FIGS. 2A and 2B are cross-sectional views of embodiments of an ostomy appliance in the form of a urostomy appliance 10 including a collecting bag 20 having an anti-reflux component 22, and configured for collection of urine from a urostomy of a user. The bag 20 includes a first exterior bag wall 24 and a second exterior bag wall 26, which walls 24, 26 are attached to each other along a peripheral attachment zone 28. A longitudinal direction of bag 20 is defined between a top end portion 30 of the bag and a bottom end portion 32 of the bag. In FIG. 1, the longitudinal direction is further indicated by longitudinal axis A-A. FIGS. 2A and 2B show embodiments wherein the urostomy appliance 10 further includes a base plate 15 for attachment of the appliance 10 to the peristomal skin of a user. The base plate 15 is connected to the first exterior bag wall 24 at an annular weld 17. FIGS. 2A and 2B further illustrate a comfort layer 19 of the urostomy appliance 10 configured to position against the skin surface of the user to increase wearing comfort for the user when the appliance 10 is worn. For illustration purposes, the view of FIG. 1 does not include (show) the base plate 15 or the comfort layer 19. The illustrated construction in FIG. 2B is not different from the one illustrated in FIG. 2A, and is included simply to illustrate the cross-section of the construction when viewed along the axis A-A of FIG. 1. FIG. 2B therefore schematically illustrates the position of the top area with its upper limit point of the center connection zone, indicated by reference number 21 in FIG. 2B. The only intended illustrative difference between the cross-sections of FIGS. 2A and 2B is therefore to indicate the presence of the center connection zone 66 (weld). It is of course to be understood that in the illustrated embodiments, the center connection 66 does not provide a closure between the sheets 50, 52 of the anti-reflux component 22. The center connection zone 66 merely connects a portion of the sheets 50, 52 to each other to form the passages 56a, 56b for stomal fluids or urine to exit through from the anti-reflux component 22 to the collecting volume 36. In embodiments as illustrated in FIG. 1, a major part 37 of the collecting volume is provided at the bottom end portion 32 of the collecting bag 20.

The first exterior bag wall 24 includes an inlet opening 34 provided at the top end portion 30 of the bag 20. The collecting volume 36 of the bag 20 is formed between the bag walls 24, 26 with a major part 37 thereof provided at the bottom end portion 32 of the bag 20. In some implementations, the top and bottom end portions of the bag 30, 32 border each other at an approximate midpoint of the bag 20, measured in the longitudinal direction of the bag.

The collecting bag 20 includes a drainage outlet 38 provided at the bottom end portion 32 of the bag. In the illustrated embodiment, the drainage outlet 38 is attached to both bag walls 24, 26 by welds 40a, 40b, and is configured to allow drainage of collected urine from collecting volume 36. The drainage outlet 38 can be opened and closed at will by the user to allow for drainage of collected urine. In the illustrated embodiment, the drainage outlet 38 includes a plug 40 attached at position 44 to a conduit portion 42 of the drainage outlet 38.

The collecting bag 20 includes an anti-reflux component 22 attached to the bag 20. In the embodiments of FIGS. 2A and 2B, the anti-reflux component 22 is attached to the first exterior bag wall 24 at weld 46 around the inlet opening 34, and to the peripheral attachment zone 28 at the top end portion 30 of the bag 20 (at position 48).

FIGS. 1 and 2A-2B illustrate embodiments of an anti-reflux component 22 provided inside a collecting bag 20. The anti-reflux component 22 is configured to prevent reflux of collected urine from the collecting volume 36 to the inlet opening 34, i.e. to hinder urine in flowing between the collecting volume 36 and the inlet opening 34.

The anti-reflux component 22 includes an interior, proximal contoured sheet 50 including a receiving opening 54, which communicates with the inlet opening 34 of collecting bag 20, and an interior, distal contoured sheet 52. In the embodiment of FIG. 1, the sheets 50, 52 of the anti-reflux component 22 are connected to each other and define two passages 56a, 56b between them, each passage 56a, 56b allowing urine to exit from the anti-reflux component 22 to the collecting volume 36. Each passage 56a. 56b has a width W in a direction transverse to the longitudinal direction of the collecting bag 20, cf. also FIG. 3.

As best seen in the view of FIG. 1, the sheets 50, 52 of the anti-reflux component 22 are connected to further define two non-linear connection zones 58a, 58b. The zones 58a, 58b extend generally in the longitudinal direction of the bag from the passages 56a, 56b, provided at a bottom edge 60 of the anti-reflux component 22 to the top end portion 30 of the bag 20. In the embodiment of FIG. 1, the non-linear connection zones 58a, 58b each define a portion of a peripheral contour 62 of the anti-reflux component 22. In FIG. 1, the non-linear connection zones 58a, 58b are shown to curve in the longitudinal direction of the bag 20, such as in arc-, and/or in 180° inverted arc-shapes in relation to each other. The arc-shapes do not necessarily describe perfect arcs. In embodiments, such as illustrated by FIG. 1, the non-linear connection zones 58a, 58b at the peripheral contour 62 of the anti-reflux component 22 provide a funnelling functionality of the anti-reflux component 22. Thereby, urine or stomal fluids entering the anti-reflux component 22 at the receiving opening 54 is guided to the passages 56a, 56b located towards the collecting volume 36 by the funnelling effect of the non-linear connection zones 58a, 58b under the influence of gravity.

In the FIG. 1 embodiment, each of the non-linear connection zones 58a, 58b extends from a bottom edge 60 of the anti-reflux component 22 to a position 64 being the same distance from the bottom edge 60 of the anti-reflux component 22 as a center C of the inlet opening 54, measured in the longitudinal direction of the bag.

In FIG. 1, the two passages 56a, 56b between the sheets 50, 52 of the anti-reflux component 22 are provided in a side-by-side relationship with each other in the transverse direction of the bag 20. The two passages 56a, 56b are separated by a center connection zone 66, in which the sheets 50, 52 of the anti-reflux component are connected to each other. Functions of the passages 56a, 56b include to readily and correctly open to allow urine or stomal fluids to pass from the anti-reflux component 22 to the collecting volume 36, while also counteracting flow of urine or stomal fluids in the opposite direction.

Figure 3:
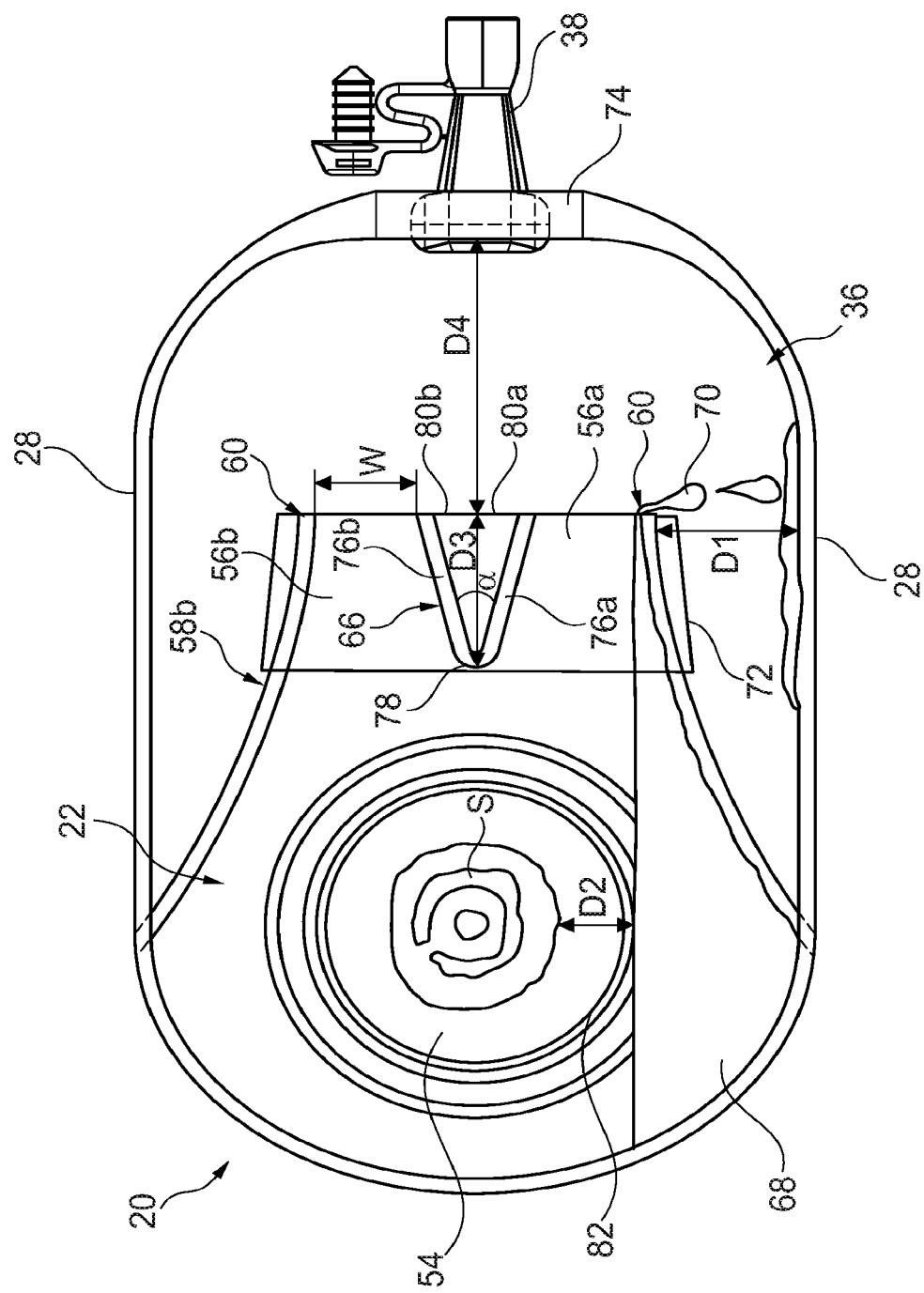
FIG. 3 is a schematic top or plan view of one embodiment of a collecting bag positioned around a stoma.

FIG. 3 is a top or plan view of one embodiment of a collecting bag 20 including an anti-reflux component 22.

FIG. 3 is a view that further schematically illustrates a situation wherein the collecting bag 20 is in use and is located around a stoma S of a user. In FIG. 3, the stoma S is a urostomy and the figure illustrates, although again schematically, a situation in which the user is lying down and a volume of urine 68 has gathered inside the anti-reflux component 22. Due to the generally horizontal position of the user's body, urine will not begin to flow into the collecting volume 36 of the collecting bag 20 via passages 56a, 56b until it has reached a predeterminable level in the anti-reflux component 22. This situation is indicated in FIG. 3 as drops of urine 70 beginning to flow "over" at the bottom edge 60 of the anti-reflux component 22 and into the collecting volume 36. The predeterminable level depends on the geometry of the collecting bag 20. In embodiments as illustrated by FIG. 3, the distance D1 between the anti-reflux component 22 at a bottom edge 60 thereof and the peripheral attachment zone 28 of the bag walls 24, 26, measured transverse to the longitudinal direction, is approximately 25 mm. Thereby, a 'reflux area' schematically indicated by trapezoid 72 is maximally distanced from the peripheral attachment zone 28 of the bag walls 24, 26. This distance effectively 'decouples' the anti-reflux component 22 from the exterior walls 34, 26 of the collecting bag 20 to the largest extent possible. This has the effect of minimizing wrinkling at the reflux area 72 of the anti-reflux component 22 caused by external forces acting on the exterior walls 24, 26 of the collecting bag 20.

Moreover, as further illustrated in the view of FIG. 3, the distance D2 should be minimized to minimize the possible urine volume gathering the in the anti-reflux component 22 and thus to make the predeterminable level of urine as low as possible. In addition, by maximizing the distance from a center point C of the inlet opening 34 and/or the receiving opening 54 to any point or portion of the peripheral contour 62 of the anti-reflux component 22, the sheets 50, 52 of the anti-reflux component will be provided with the greatest possible degree of freedom to move (without being constrained by connecting zones/welds). This in turn ensures as much space as possible for a protruding stoma reaching into the collecting bag 20 and into the inside of the anti-reflux component 22. Thereby, any risk of the stoma interfering with, or being obstructed by, the sheets 50, 52 of the anti-reflux component 22, is minimized.

In embodiments as illustrated, a longitudinal extent D3 of the center connection zone 66 is around 28 mm. The greater the longitudinal extent D3 of the center connection zone 66, the greater security against backflow the 'reflux area' 72 creates. In embodiments, a distance D4 between the bottom edge 60 of the anti-reflux component and a portion of the peripheral attachment zone 74 at or adjacent the drainage outlet 38 is at least 52 mm.

In embodiments as illustrated, the center connection zone 66 has a greatest extent transverse to the longitudinal direction at the bottom edge 60 of the anti-reflux component 22 and gradually decreases in transverse extent towards the top end portion 30 of the bag 20. In the illustrated embodiments, the center connection zone 66 includes two legs 76a, 76b defined with an angle α between them. The legs 76a, 76b meet in a top area 78 forming an upper limit point of the center connection zone 66. The angle α between the legs 76a, 76b is acute. At the bottom edge 60 of the anti-reflux component 22, the legs 76a, 76b of the center connection zone 66 terminate in bottom limit points 80a, 80b with a distance between them. In embodiments as illustrated by FIG. 3, the sheets 50, 52 of the anti-reflux component 22 at the center connection zone 66 are connected to each other only by (at) the legs 76a, 76b.

In embodiments as illustrated by the view of FIG. 3, a width W of each the passages 56a, 56b is around 18 mm. This width ensures a good flow of urine from the anti-reflux component 22 and into the collecting volume 36 of a urostomy collecting bag while simultaneously not being excessively or unnecessarily wide. Moreover, the width W in combine with distances D1 and D2 to ensure that each of the passages (in FIG. 3 it is passage 56a) creates a wide enough clearance for urine 68 to begin flowing into the collecting volume 36, before the level of urine gathering inside the anti-reflux component 22 rises 'above' the inner periphery 82 of the receiving opening 54 and reaches the stoma S. In embodiments, each of the passages can accommodate two urinary catheters of French size 10.

Figure 4:
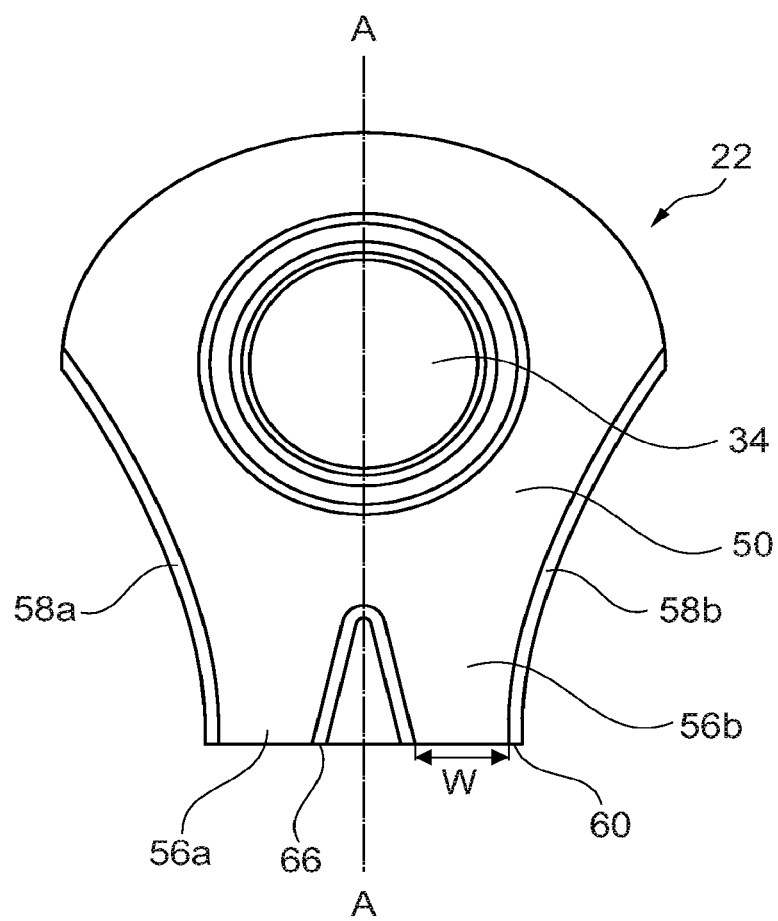
FIG. 4 is a schematic top or plan view of one embodiment of an anti-reflux component.

FIG. 4 is a schematic top plan view of one embodiment of an anti-reflux component 22. The anti-reflux component 22 is suitable for use in different types of collecting bags for collecting stomal fluids, particularly for bags for collecting urine from a urostomy.

The anti-reflux component 22 is configured to prevent reflux of collected fluids from a collecting volume to an inlet opening of a collecting bag, and includes a first contoured sheet 50 including a receiving opening 34 for communicating with an inlet opening of the collecting bag. The anti-reflux component 22 further includes a second contoured sheet 52, the contoured sheets 50, 52 being connected to each other to define two passages 56a, 56b between them towards an exterior of the anti-reflux component 22. The passages 56a, 56b have a width W in a transverse direction of the anti-reflux component. The anti-reflux component 22 further includes two or more non-linear connection zones 58a, 58b extending from the passages 56a, 56b to a position being the same distance from a bottom edge 60 of the anti-reflux component as the receiving opening 34, measured in a longitudinal direction of the anti-reflux component 22 (along axis A-A).

The effects and advantages of the anti-reflux component 22 and its components are described above in relation to the first aspect of the disclosure and apply in a similar manner to the anti-reflux component 22 according to the second aspect.

Although particular features have been shown and described, it will be understood that they are not intended to limit the claimed invention, and it will be made obvious to those skilled in the art that various changes and modifications may be made without departing from the scope of the claimed invention. The specification and drawings are, accordingly to be regarded in an illustrative rather than restrictive sense. The claims are intended to include alternatives and modifications within the scope of the invention.

The invention claimed is:

1. An ostomy appliance comprising:
    a waste collection container provided by a first wall sealed around a periphery to a second wall to form a collection volume inside of the waste collection container, with a longitudinal direction extending from a top end portion to a bottom end portion of the waste collection container;
    an inlet opening formed through the first wall, with the inlet opening having a center and sized for placement around a stoma;
    a drainage outlet provided on the bottom end portion of the waste collection container and adapted to drain body waste from the waste collection container; and an anti-reflux component disposed inside of the waste collection container, with the anti-reflux component comprising:
  a first sheet having an aperture sealed around the inlet opening of the first wall,
  a second sheet connected to the first sheet along a first lateral connection zone on a first side and along a second lateral connection zone on an opposing second side of the anti-reflux component,
wherein the first sheet and the second sheet of the anti-reflux component are connected to the top end portion of the waste collection container only above the center of the inlet opening.

2. The ostomy appliance of claim 1, wherein the anti-reflux component further comprises:
  a third connection zone formed between the first sheet and the second sheet to form a first passage and a separate second passage that open to a bottom edge of the anti-reflux component.

3. The ostomy appliance of claim 1, wherein the first lateral connection zone and the second lateral connection zone of the anti-reflux component are not connected to the waste collection container.

4. The ostomy appliance of claim 1, wherein the anti-reflux component extends longitudinally from the top end portion of the waste collection container to a bottom edge of the anti-reflux component, and the first lateral connection zone and the second lateral connection zone of the anti-reflux component are decoupled from the waste collection container from the center of the inlet opening to the bottom edge of the anti-reflux component.

5. The ostomy appliance of claim 1, wherein the first wall and the second wall of the waste collection container are exterior walls of the ostomy appliance.

6. The ostomy appliance of claim 1, wherein the first lateral connection zone and the second lateral connection zone have a non-linear curvature and taper a lateral width of the anti-reflux component to be most narrow when measured laterally across a bottom edge of the anti-reflux component.

7. The ostomy appliance of claim 1, wherein the first lateral connection zone and the second lateral connection zone taper to provide the anti-reflux component with a funnel-shape that is wider at the inlet opening and narrower at a bottom edge of the anti-reflux component.

8. The ostomy appliance of claim 1, wherein the waste collection container is a urostomy bag sized for use with an infant user.

9. The ostomy appliance of claim 1, further comprising a plug insertable into the drainage outlet.

10. The ostomy appliance of claim 1, wherein the anti-reflux component further comprises a connection formed between the first sheet and the second sheet to form two passages provided in a side-by-side relationship that open to a bottom edge of the anti-reflux component.

11. The ostomy appliance of claim 1, wherein the first lateral connection zone and the second lateral connection zone extend to a bottom edge of the anti-reflux component, and the bottom edge of the anti-reflux component is spaced the periphery of the waste collection container.

12. An ostomy appliance comprising:
  a first bag and a second bag, with the first bag comprising:
    a first wall sealed around a periphery to a second wall to form a waste collection volume, with a longitudinal direction extending from a top end portion to a bottom end portion of the first bag,
    an inlet opening formed through the first wall, with the inlet opening having a center and sized for placement around a stoma,
    a drainage outlet provided on the bottom end portion of the first bag and adapted to drain the waste collection volume;
  the second bag is disposed inside of the first bag, the second bag comprising:
    a first sheet having an aperture sealed around the inlet opening in the first wall of the first bag,
    a second sheet connected to the first sheet along a first lateral connection zone on a first side and along a second lateral connection zone on an opposing second side of the second bag;
  wherein the first sheet and the second sheet of the second bag are connected to the top end portion of the first bag only above the center of the inlet opening.

13. The ostomy appliance of claim 12, wherein the second bag is an anti-reflux valve having a bottom edge that is spaced apart from the bottom end portion of the first bag;
wherein, when liquid is contained within the waste collection volume of the first bag, the anti-reflux valve is adapted to allow a level of the liquid to rise above the bottom edge while preventing the liquid from entering the inlet opening.

14. The ostomy appliance of claim 13, wherein the second bag further comprises a connection formed between the first sheet and the second sheet to form two passages provided in a side-by-side relationship that open to the bottom edge of the anti-reflux component.

* * * * *